US007872171B2

(12) United States Patent
Webb

(10) Patent No.: US 7,872,171 B2
(45) Date of Patent: *Jan. 18, 2011

(54) QUANTITATIVE TRAIT LOCI ASSOCIATED WITH SOYBEAN CYST NEMATODE RESISTANCE AND USES THEREOF

(75) Inventor: David M. Webb, Zionsville, IN (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 1342 days.

This patent is subject to a terminal disclaimer.

(21) Appl. No.: 10/352,418

(22) Filed: Jan. 28, 2003

(65) Prior Publication Data

US 2003/0135881 A1 Jul. 17, 2003

Related U.S. Application Data

(63) Continuation of application No. 09/542,500, filed on Apr. 3, 2000, now Pat. No. 6,538,175, which is a continuation-in-part of application No. 08/876,104, filed on Jun. 13, 1997, now Pat. No. 6,162,967, which is a continuation-in-part of application No. 08/551,872, filed on Oct. 24, 1995, now abandoned.

(51) Int. Cl.
*A01H 1/04* (2006.01)
*A01H 1/02* (2006.01)
(52) U.S. Cl. .................. 800/267; 800/260; 800/265
(58) Field of Classification Search ............... 800/260, 800/266, 267, 312, 265
See application file for complete search history.

(56) References Cited

U.S. PATENT DOCUMENTS 5,491,081 A * 2/1996 Webb .................... 800/267
6,162,967 A * 12/2000 Webb .................... 800/312
6,300,541 B1 10/2001 Lightfoot et al.
6,538,175 B1 * 3/2003 Webb .................... 800/265
7,154,021 B2 12/2006 Hauge et al.

OTHER PUBLICATIONS

Lee et al. 1996. Theor. Appl. Genet. 92: 516-523.*
van Ooijen et al. 1996. Theor. Appl. Genet. 89: 1007-1013.*
Concibido et al. 1997. Crop Sci. 37: 258-264.*
Cregan et al. 1999. Theor. Appl. Genet. 99: 811-818.*
Concibido et al. 1995. Soybean genetics newsletter 22: 269-272.*
Concibido et al, Soybean Genetics Newsletter 20: 136-139, May 1993.*
Baltazar et al, Soybean Genetics Newsletter 19: 120-122, Apr. 1992.*
Boutin et al, Soybean Genetics Newsletter 19: 123-127, Apr. 1992.*
Boutin et al. Soybean Genetics Newsletter 19: 123-127, 1992.*
Tanksley et al. Biotechnology 7: 257-264, 1989.*
Concibido et al. Soybean Genetics Newsletter 20: 136-139, 1993.*
Ferreira et at. Plant Mol Biol Reporter 15: 335-354, 1997.*
Webb et al. 1995. Theor. Appl. Genet. 91: 574-581.*
Concibido et al. 1993. Soybean Genetics Newsletter 20: 136-139.*
Boutin et al. 1992. Soybean Genetics Newsletter 19: 123-127.*
Keim et al. 1990. Genetics 126: 735-742.*
Mansur, et al., 1993, *Theoretical and Applied Genetics*, 86(8): 914-918, "Determining the linkage of quantitative trait loci to RFLP markers using extreme phenotypes of recombinant inbreds of soybean".
Mansur, et al., 1993, *Theoretical and Applied Genetics*, 86(8): 907-913, "Interval mapping of quantitative trait loci for reproductive, morphological, and seed traits of soybean".
Diers, et al., 1992, *Journal Plant Nutrition*, 15(10): 2127-2136, "Possible identification of quantitative trait loci affecting iron efficiency in soybean".
Diers, et al., 1992, *Theoretical and Applied Genetics*, 83(5): 608-612, "RFLP analysis of soybean seed protein and oil content".
Keim, et al., 1990, *Theoretical and Applied Genetics*, 79(4): 465-469, "Genetic analysis of soybean hard seededness with molecular markers".
Lark, et al., 1994, Theoretical and Applied Genetics, 88(3-4): 486-489, "Epistatic expression of quantitative trait loci (QTL) in soybean determined by QTL association with RFLP alleles".
Diers, B, et. al. "Possible Identification of Quantitative Trait Loci Affecting Iron Efficiency in Soybean", Journal of Plant Nutrition, 15(10), 2127-2136 (1992).
Matson, A.L., and L.F. Williams. 1965. Evidence of a fourth gene for resistance to the soybean cyst nematode. Crop Sci. 5:477.
Weisemann, J., "Molecular markers located proximal to the soybean cyst nematode resistance gene, Rhg 4" Theor. Appl. Genet. 85:136-138 (1992).
Concibido, V. et. al. "DNA Marker Analysis of Loci underlying Resistance to Soybean Cyst Nematode (*Heterodera glycines* Ichinohe)." Crop. Sci. 34:240-246 (1994).
Kabelka, E, et. al. "Glycine soja PI 468916 SCN Resistance Loci's Associated Effects on Soybean Seed Yield and Other Agronomic Traits", Crop Sci. 46: 622-629 (2006).
Wang, D, et. al. "Loci underlying resistance to Race 3 of soybean cyst nematode in Glycine soja plant introduction 468916.", Theor Appl Genet. 103: 561-566 (2001).
E-mail message from David Webb to David Lightfoot of GAAB dated Jul. 9, 1993 regarding a master's project to be funded by Pioneer.
E-mail message from Keim to Lightfoot dated May 5, 1993.
RFLP mapping of cyst nematode resistance genes in soybeans. By: Concibido, V.; Soybean Genetics Newsletter 20, 1993, p. 136-139 (Journal article) and note regarding information on RFLP markers linked to SCN resistance.
Iowa State University, USDA-ARS, Soybean AFLP Map, Apr. 22, 1991.

(Continued)

*Primary Examiner*—Medina A. Ibrahim
*Assistant Examiner*—Keith O. Robinson

(57) ABSTRACT

A method for selecting a soybean cyst nematode resistant plant by marker assisted selection of quantitative trait loci associated with soybean cyst nematode resistance. The method employs nucleic acid markers genetically linked to quantitative trait loci to select the soybean cyst nematode resistant plant. Methods for identifying quantitative trait loci associated with soybean cyst nematode resistance in a plant.

4 Claims, 6 Drawing Sheets

OTHER PUBLICATIONS

Ruben, E, et. al. "Genomic Analysis of the rfg1 Locus: Candidate Genes That Underlie Soybean Resistance to the Cyst Nematode." Mol. Gen Genomics DOI 10.1007/s00438-006-150-8 (2006).

Triwitayakorn, K, et. al. "Genomic Analysis of a Region Encompassing QRfs1 and QRfs2: Genes That Underlie Soybean Resistance to Sudden Death Syndrome." Genome 48: 125-138 (2005).

Printout Dated Jan. 23, 2007 of Figure 1 from the Soybean GBrowse database Version 4.

Afzal, Ahmed, et. al. "Soybean Disease Resistance Protein RHG1-LRR domain Expressed, Purified and Refolded From *Escherichia coli* Inclusion Bodies: Preparation for a Functional Analysis." Protein Expression & Purification (2007) doi:10.1016/j.pep.2006.12.017.

Title page, Thesis approval page, List of appendix tables and selected tables (2A) and figures (1B and 5B) from a master's thesis by Hnetkovsky, N. "Soybean Sudden Death Syndrome Resistance Genes Mapped by Molecular Markers" Southern Illinois University, Aug. 1994.

Concibido, V. "Identification and Characterization of Soybean Cyst Nematode Resistance Genes Using DNA Markers." University of Minnesota, Oct. 1995.

Boutin et. al., Soybean Genetics Newsletter 19: 123-127, 1992.

Webb, D, "Genetic Mapping of Soybean Cyst Nematode Race-3 Resistance Loci in the Soybean PI 437.654", Theor Appl Genet (1995) 91: 574-581.

\* cited by examiner

QUANTITATIVE TRAIT LOCI ASSOCIATED WITH SOYBEAN CYST NEMATODE RESISTANCE AND USES THEREOF

CROSS REFERENCE TO RELATED APPLICATIONS

This application is a continuation of U.S. Ser. No. 09/542,500, now issued as U.S. Pat. No. 6,538,175, which is a continuation of U.S. Ser. No. 08/876,104, now issued as U.S. Pat. No. 6,162,967, which is a continuation of Ser. No. 08/551,872 (abandoned). This application claims priority to each of these prior applications.

FIELD OF THE INVENTION

This invention relates to the cloning of genes for resistance to soybean cyst nematode.

BACKGROUND OF THE INVENTION

Soybeans are a major cash crop and investment commodity in North America and elsewhere. Soybean oil is one of the most widely used edible oils, and soybeans are used worldwide both in animal feed and in human food production.

The soybean cyst nematode (SCN) (*Heterodera glycines* Ichinohe) causes substantial yield loss in North American soybean [*Glycine max* (L.) Merr.] (Mulrooney 1988). *Heterodera glycines* Ichinohe, was first identified on soybeans in the United States in 1954 at Castle Hayne, N.C. Winstead, et al., Plant Dis. Rep. 39:9-11, 1955. Since its discovery the soybean cyst nematode ("SCN") has been recognized as one of the most destructive pests in soybean. It has been reported in nearly all states in which soybeans are grown, and it causes major production problems in several states, being particularly destructive in the midwestern states. See generally: Calwell, et al., Agron. J. 52:635-636, 1960; Rao-Arelli and Anand, Crop. Sci. 28:650-652, 1988; Baltazar and Mansur, Soybean Genet. Newsl. 19:120-122, 1992; Concibido, et al., Crop. Sci., 1993. For example, susceptible soybean cultivars had 6-36% lower seed yields than did resistant cultivars on SCN race-3 infested sites in Iowa (Niblack and Norton 1992).

Although the use of nematocides is effective in reducing the population level of the nematode, nematocide use is both uneconomical and potentially environmentally unsound as a control measure in soybean production. Neither is crop rotation a practical means of nematode control, since rotation with a nonsusceptible crop for at least two years is necessary for reducing soybean losses. Therefore, it has long been felt by soybean breeders, that use of resistant varieties is the most practical control measure.

Screening of soybean germplasm for resistance to SCN was begun soon after the discovery of the nematode in the United States, and Golden, et al. (Plant Dis. Rep. 54:544-546, 1970) have described the determination of SCN races. Although SCN was discovered in North America about 40 years ago, soybean breeding for resistance to SCN has mostly utilized genes from two plant introductions—Peking and PI88788, and while these lines have resistance genes for several SCN races, including race-3, they do not provide resistance to all known races.

The plant introduction PI 437.654 is the only known soybean to have resistance to SCN races-3 (Anand 1984), 1, 2, 5, 14 (Anand 1985), 6, and 9 (Rao-Arelli et al. 1992b). However, PI 437.654 has a black seed coat, poor standability, seed shattering, and low yield, necessitating the introgression of its SCN resistance into elite germplasm with a minimum of linkage drag. Conventional breeding with PI 437.654 produced the variety 'Hartwig' (Anand 1991), which is more adapted to cultivation and can be used as an alternative source of SCN resistance in soybean breeding programs.

Resistance to SCN is multigenic and quantitative in soybean (Mansur et al. 1993), though complete resistance can be scored qualitatively. For complete resistance to SCN, PI 437.654 has two or three loci for race-3, two or four loci for race-5, and three or four loci for race-14 (Myers and Anand 1991). The multiple genes and SCN races involved contribute to the difficulty breeders have in developing SCN resistant soybean varieties.

Breeding programs for SCN resistance rely primarily on field evaluations where natural nematode populations occur. However, these populations can be mixtures of undetermined races (Young 1982) and the environment can affect the overwintering and infection capability of the nematodes (Niblack and Norton 1992). Although evaluations using inbred nematode populations in controlled greenhouse environments are superior, they are prohibitively expensive and the nematodes are difficult to manage for large breeding programs (Rao-Arelli, pers comm). These deficiencies in each evaluation method make SCN resistance a difficult trait to manipulate in soybean improvement programs.

DEPOSIT STATEMENT

A deposit of the Pioneer Hi-Bred International, Inc. proprietary nucleic acid markers disclosed above and recited in the appended claims has been made with the American Type Culture Collection (ATCC), 12301 Parklawn Drive, Rockville, Md., 20852. The dates of deposit were Oct. 19, 1995 and Jul. 8, 1997. The markers deposited were taken from the same deposit maintained by Pioneer Hi-Bred International, Inc. since prior to the filing date of this application. All restrictions upon the deposit have been removed, and the deposit is intended to meet all of the requirements of 37 C.F.R. §1.801-1.809. The markers deposited and their respective ATCC accession numbers are as follows: php02366 assigned ATCC 69934; php02340 assigned ATCC 69935; php02361 assigned ATCC 69936; php02301 assigned ATCC 69937; php05180 assigned ATCC 69938; php02275 assigned ATCC 69937; php02302 assigned ATCC 69940; php05354 assigned ATCC 98495; and php05219 assigned ATCC 98490. The deposit will be maintained in the depository for a period of 30 years, or 5 years after the last request, or for the effective life of the patent, whichever is longer, and will be replaced as necessary during that period.

Genetic markers closely linked to important genes may be used to indirectly select for favorable alleles more efficiently than direct phenotypic selection (Lande and Thompson 1990). The i allele at the I locus is responsible for black or imperfect black seed-coat type, and is a morphological genetic-marker closely linked in coupling to the SCN resistance allele, $Rhg_4$, in the variety Peking (Matson and Williams 1965). The I locus is mapped to linkage group VII of the classical genetic map (Weiss 1970) and to linkage group A of a public RFLP map (Keim et al. 1990). SCN race-3 resistance loci are also associated with RFLP markers mapped to linkage groups A, G and K in the soybean PI 209.332 (Concibido et al. 1994).

Therefore, it is of particular importance, both to the soybean breeder and to farmers who grow and sell soybeans as a cash crop, to identify, through genetic mapping, the quantitative trait loci (QTL) for resistance to the various SCN races. Knowing the QTLs associated with resistance to the SCN races, soybean breeders will be better able to breed SCN resistant soybeans which also possess the other genotypic and phenotypic characteristics required for commercial soybean lines.

SUMMARY

Therefore, loci in PI 437.654 were genetically mapped to linkage groups A2, C1, G, L25, and L26 and together gave complete resistance to SCN races 1, 2, 3, 5, and 14. Another locus on group M was involved with resistance in that it did not segregate independently from the SCN resistance allele on group G. Markers linked to these loci may be used for marker-assisted selection during the introgression of SCN resistance from PI 437.654 or other sources into elite soybean.

The present invention provides a method of introgressing SCN resistance into non-resistant soybean germplasm. Loci associated with SCN resistance in soybean lines known to be resistant to SCN are used in marker assisted selection during introgression of SCN resistance into elite soybean germplasm. Examples of soybean lines known to be resistant to one or more races of SCN include PI437.654, Peking, and PI90763. The method of the present invention can be used to breed soybeans resistant to any SCN race. The SCN races of particular commercial importance are races-3, 1, 2, 5, 14, 6 and 9.

The method of the present invention comprises the use of nucleic acid markers genetically linked to loci associated with SCN resistance in lines known to be resistant to one or more SCN races. The markers are used in genetic mapping of genetic material of soybean lines to be used in and/or which have been developed in a breeding program, allowing for marker-assisted selection during introgression of SCN resistance into elite germplasm.

According to the method of the invention, any art-recognized genetic mapping techniques may be utilized, with preferred embodiments utilizing Restriction Fragment Length Polymorphism (RFLP) mapping, RAPD mapping, or microsatellite mapping, using the nucleic acid markers recognized or applicable to the particular method(s). Markers useful in genetic mapping include, for example, the following: pA85a, php02302a, php02340a, pK400a, pT155a, pBLT24a, pBLT65a, php05180a, pSAC3a, pA1116, php05266a, php022986, pA664a, pA63a, php02366a, php02361a, php05354a, php05219a, pK69a, pL50c, pK18a, pA567a, pA407a, pA4046, pA226a, pA715a, pK24a, pB157b, php02275a, php05278a, php05240c, pBLT49a, pK79a, and php03488a. These, and equivalent markers linked to SCN resistance QTL, can be used in positional cloning of genes located within those QTL.

DETAILED DESCRIPTION

The present invention relates to a novel and useful method for introgressing, in a reliable and predictable manner, SCN resistance into non-resistant soybean germplasm. The method involves the genetic-mapping of loci associated with SCN resistance. SCN race resistance can be determined in any acceptable manner; preferably in greenhouse conditions using a homogenous population of the particular SCN race.

The soybean line selected for mapping is subjected to DNA extraction. In a preferred embodiment the CTAB method (Murray and Thompson, Nucl. Acids Rev. 8:4321-4325, 1980; Keim et al., Soybean Genet. Newsl. 15:150-152, 1988) is used. Nucleic acid probes are used as markers in mapping the resistance loci, and appropriate probes are selected based upon the mapping method to be used. The probes can be either RNA or DNA probes, and mapping is performed using a number of methods recognized in the art, including, for example, AFLP, RFLP, RAPD, or microsatellite technology.

Figure 1:
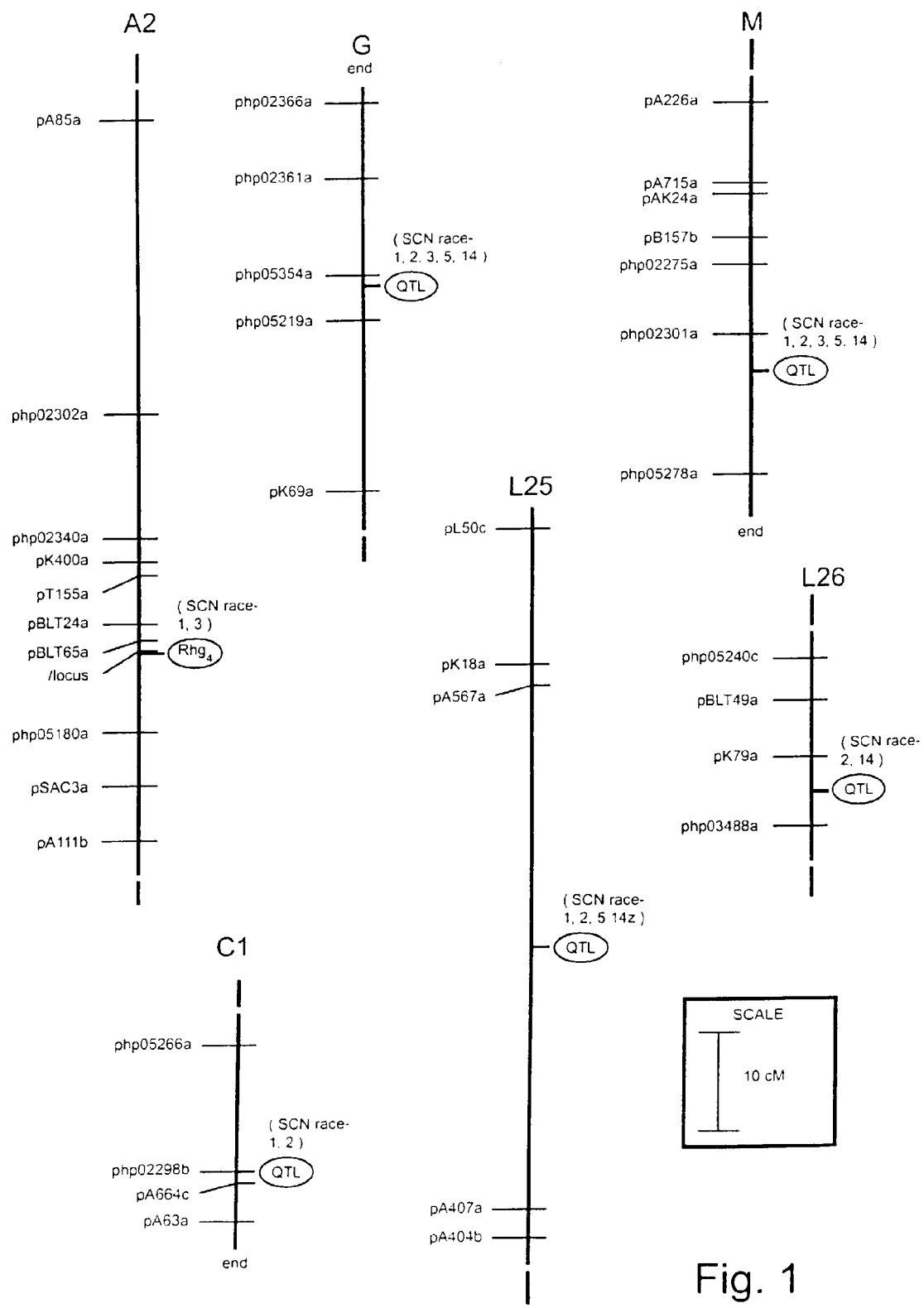
FIG. 1 shows approximate locations of RFLP markers and QTL associated with SCN resistance found in PI 437.654 on linkage groups A2, C1, G, M, L25, and L26, respectively. Marker names are on the left of each linkage group. Genetic distances (cM) were from the recombinant-inbred function of MAPMAKER/EXP 3.0.

In a particular embodiment, DNA probes are used for RFLP markers. Such probes can come from, for example, Pst I-cloned genomic libraries, and the cloned inserts used as probes may be amplified, for example by PCR, LCR, NASBA™, or other amplification methods recognized in the art. For example, the markers useful in a preferred embodiment of the invention include the following: pA85a, php02302a, php02340a, pK400a, pT155a, pBLT24a, pBLT65a, php05180a, pSAC3a, pA1116, php05266a, php022986, pA664a, pA63a, php02366a, php02361a, php05354a, php05219a, pK69a, pL50c, pK18a, pA567a, pA407a, pA4046, pA226a, pA715a, pK24a, pB157b, php02275a, php05278a, php05240c, pBLT49a, pK79a, and php03488a. FIG. 1 shows the linkage groups with which the foregoing probes are associated. The Pioneer Hi-Bred International, Inc. proprietary nucleic acid markers have been deposited with the ATCC and are available as follows: php05354 assigned ATCC 98495; php05219 assigned ATCC 98490; php02366 assigned ATCC 69934; php02340 assigned ATCC 69935; php02361 assigned ATCC 69936; php02301 assigned ATCC 69937; php05180 assigned ATCC 69938; php02275 assigned ATCC 69937; and php02302 assigned ATCC 69940. The other, non-proprietary probes are available from Linkage Genetics, Salt Lake City, Utah, and from Biogenetic Services, Brookings, S. Dak.

For RFLP mapping, restriction fragments are generated using specific restriction enzymes, and the digestion, electrophoresis, Southern transfers and nucleic acid hybridizations are conducted according to art-recognized techniques. See, e.g., Keim et al., Theor. Appl. Genet. 77:786-792, 1989, the disclosure of which are hereby incorporated herein by reference.

In an alternative embodiment of the method of the invention, RAPD technology can be utilized for genetic mapping. A DNA preparation is amplified using art-recognized amplification techniques, and suitable nucleic acid markers are used. Alternatively, other genetic mapping technologies recognized in the art can be used in the practice of the present invention.

In a soybean breeding program, the method of the present invention envisions the use of marker-associated selection for one or more loci at any stage of population development in a two-parent population, multiple parent population, or a backcross population. Such populations are described in Fehr, W. R. 1987, Breeding Methods for Cultivar Development, in J. R. Wildox (ed.) Soybeans: Improvement, Production, and Uses, 2d Ed., the disclosures of which are hereby incorporated herein by reference.

Marker-assisted selection according to art-recognized methods may be made, for example, step-wise, whereby the different SCN resistance loci are selected in more than one generation; or, as an alternative example, simultaneously, whereby all three loci are selected in the same generation. Marker-assisted selection for SCN resistance may be done before, in conjunction with, or after testing and selection for other traits such as seed yield.

The DNA from target populations may be obtained from any plant part, and each DNA sample may represent the genotype of single or multiple plant individuals (including seed).

Marker-assisted selection may also be used to confirm previous selection for SCN race-3 resistance or susceptibility made by challenging plants with soybean cyst nematodes in the field or greenhouse and scoring the resulting phenotypes.

The following examples offered by way of illustration and not by way of limitation.

Example 1

Materials and Methods

Germplasm Development and Characteristics

A population of 328 recombinant-inbred lines (RILs) was licensed by Pioneer Hi-Bred International, Inc. from Iowa State University and used in this study. This population originated from a cross between two soybean G. max lines, PI 437.654 and BSR101, and was developed by single-seed-descent inbreeding from the $F_2$ to the $F_{6:7}$ generation (Baltazar and Mansur 1992; Keim et al. 1994). Pi 437.654 is a plant introduction from China in the USDA soybean germplasm collection received from the USSR in 1980 (Nelson et al. 1988). It is in Maturity Group III and is resistant to all known races of SCN. BSR101 was developed at Iowa State University and is in Maturity Group I and is susceptible to SCN (Tachibana et al. 1987). At the I locus, PI 437.654 carries the i allele for black or imperfect black seed, and BSR101 carries the $i^i$ allele for yellow or green seed. The RIL population for these alleles was scored and the/locus was mapped as a marker.

Laboratory Methods

DNA of soybean material was extracted using a CTAB method (Murray and Thompson 1980; Keim et al. 1988), with the following modifications. Lyophilized tissue was powdered by adding 2.5 g of glass beads (Fisher cat. #11-312A) and 750 mg of tissue in a 50 mL tube and shaking in a paint-can shaker. The concentration of CTAB (hexadecyltrimethyl-ammonium bromide) in the extraction and precipitation buffers was reduced from 1% to 0.5%. After the DNA was precipitated with CTAB, the DNA pellet was dissolved in 2 mL 1 M NaCl with shaking at 65° C., 200 rpm, for 2-3 hr. The DNA was re-precipitated by adding 4.5 mL ice-cold 95% EtOH. The spooled DNA was washed with 1 mL of 65%, then 1 mL of 85% EtOH, to further remove salts. After the EtOH washes, the DNA was dissolved in 500-1000 uL TE (10, 1), diluted to 500 ng $uL^{-1}$, and stored at 4° C. until required.

Most RFLP markers used were from PstI-cloned genomic libraries and were either public (Keim and Shoemaker 1988) or proprietary (prefixed php) to Pioneer Hi-Bred Int. Some RFLP markers used were from USDA-ARS (Beltsville, Md.) cDNA clones (prefixed pBLT). The cloned inserts used as probes were amplified by polymerase chain reaction using oligonucleotide primers of the $T_3$ and $T_7$ promoter regions of the phagemid vector $pBS^{+/-}$. The restriction enzymes EcoRI, HindIII, EcoRI, DraI, TaqI, and HaeIII were employed to digest the parental and population DNA. Approximately 900 RFLP markers were used against PI 437.654 and BSR101 to identify and map 355 RFLP markers segregating in the RIL population. The DNA digestions, electrophoresis, Southern transfers, and DNA hybridizations were conducted as described previously (Keim et al. 1989).

Soybean Cyst Nematode Race Isolates

Each SCN race isolate used in this study was collected from the field or obtained from other researchers, increased, and maintained in a greenhouse by staff at the Department of Agronomy, University of Missouri, Delta Center, P.O. Box 160, Portageville, Mo., 63873. The race scheme used was based on that of Riggs and Schmitt (1988).

The SCN race-1 isolate was collected from soil in Washington County, North Carolina and reproduced on the cultivar, 'Essex', for 10-12 generations and tested against a set of the standard soybean host differentials; Peking, PI 90763, 'Pickett', and PI 88788. The population gave a typical race-1 response on the differentials.

The SCN race-2 isolate was collected from soil in Beauford County, North Carolina and reproduced on the cultivar Pickett. It gave a typical race-2 response on the differentials.

The SCN race-3 isolate was collected from soil at the Ames Plantation, near Grand Junction, Tenn. (courtesy of Dr. L. D. Young, USDA-ARS, Jackson, Tenn.). This isolate was increased and maintained for approximately 60 generations on roots of the cultivar, Essex, and gave a typical race-3 response on the differentials.

The SCN race-5 isolate was collected from soil at the University of Missouri Rhodes Farm near Clarkton, Mo. This isolate was increased and maintained on the variety PI 88788, and gave a typical race-5 response on the differentials.

The SCN race-14 isolate was collected from soil in Obion County, Tennessee. This isolate was increased and maintained on a mixture of plants from the varieties 'Forrest', Peking, and PI90763; and gave a typical race-14 response on the differentials.

Soybean Cyst Nematode Screening

The $F_{6:7}$ RILs of the PI 437.654 X BSR101 population were evaluated against each SCN race in batches of 300 plants plus the five host differentials in a greenhouse at the Delta Center, University of Missouri, Portageville. Five or ten seeds per line were planted and SCN infection rates were based on cyst counts from the plants that emerged and survived, with at least three plants per line required to obtain a mean score. The numbers of lines and seeds planted per line for each SCN race are shown in Table 1. The inoculation and evaluation methods were as previously described (Rao-Arelli and Anand 1988; Rao-Arelli et al. 1991 b). Thirty days after inoculation, plant roots were washed and the dislodged white females were counted under a stereomicroscope.

To minimize the environmentally caused variation in cyst counts among the different batches of lines, an index-of-parasitism (IP) was calculated for each RIL as a percentage of the cysts on plants of the susceptible control variety Essex (for SCN races-3, -5, and -14) or Hutcheson (for SCN races-1 and -2) grown at the same time and under the same conditions.

$$IP = \frac{\text{Avg. No. of cysts per } RIL}{\text{Avg. No. of cysts per control}} \times 100$$

For QTL analyses, the IP scores were transformed using the natural-log function as follows.

$$IP \ln = Ln(IP+1)$$

The number 1 was added to each IP score to exclude negative numbers from the transformed data set. The purpose of this transformation was to correct for unequal error variances among marker classes because the variances were dependent upon the magnitude of the means (Box and Draper 1987).

Data Analyses

Genetic linkages and distances between markers were estimated by maximum likelihood analysis of segregating RFLP-marker patterns in the RIL population, using the computer program MAPMAKER/EXP 3.0 (Lincoln et al. 1993) and a mapping protocol similar to one described by Landry et al. (1991). Centimorgan distances shown in FIG. 1 were considered comparable to those that would be obtained using an $F_2$ population.

The genome was initially scanned for QTL by calculating likelihood statistics (LOD scores) based on an additive genetic model at each marker locus using MAPMAKER/QTL (Lincoln and Lander 1990). Based upon Lander and Botstein's simulations (1989) and the genome size and density of marker loci used in the present experiment, it was decided prior to analyses that a LOD score of 3.0 was an appropriate threshold for declaring linkage of a marker with a QTL. However, a comparison of scans among the traits for the five different SCN races revealed regions that had elevated LOD scores (>1.0) for multiple traits. Markers in such regions were included in the simultaneous analyses.

Interval mapping (Lander and Botstein 1986) with MAPMAKER/QTL to estimate the positions of QTL relative to their nearby markers was performed with maximum-likelihood tests at positions every 2 cM between adjacently linked markers.

Unlinked markers might explain some of the same phenotypic variability. To decrease bias from such multi-colinear data or from unbalanced data (Knapp et al. 1992) and assess interaction effects (epistasis) among QTL, the markers that had the highest LOD score in genomic regions that exceeded the 1.0 LOD threshold were evaluated simultaneously, using linear models that accommodate multiple marker loci and their interactions:

$$Y_{i(g)} = \mu + M_g + I(M)_{i(g)}, \quad (2)$$

where $Y_{i(g)}$ is the IP score for recombinant inbred line i nested in genotype g, $\mu$ is the mean, g=1, 2, 3 . . . G and is an index of the genotypic class for the marker loci and their interaction effects $M_g$, and $I(M)_{i(g)}$ are the random effects of RI line i within genotypic class g.

$$M_g = \sum_m q_g(m) + \pi_{m<m'} q_g(m) q_g(m') + \pi_{m<m'<m''} q_g(m) q_g(m') q_g(m'') + K$$

for m=1, 2, 3 . . . marker loci, where g is an index of the genotypic class at marker locus m arbitrarily designated as having zero or two alleles from PI 437.654, and $q_{g(m)}$ represents the genetic effects of the QTL detected at marker locus m.

Results

The ranges and means of IP scores and the parental IP scores for all five SCN-race screenings are shown in Table 1.

TABLE 1

The number of lines screened, the number of seeds per line planted, the range and means of IP scores for the population, and the parental IP scores for each SCN screening.

| SCN Race | No. lines tested | No. seeds per line | IP range | IP mean | PI 437.654 IP | BSR101 IP |
|---|---|---|---|---|---|---|
| 1 | 324 | 5 | 0-130 | 37 | 0 | 42 |
| 2 | 308 | 5 | 0-156 | 51 | 0 | 75 |
| 3 | 298 | 10 | 0-214 | 47 | 0 | 51 |
| 5 | 200 | 10 | 0-126 | 53 | 0 | 66 |
| 14 | 287 | 5 | 0-103 | 33 | 0 | 48 |

Identification of SCN Resistance Loci

Six significant loci or QTL associated with SCN resistance on the independent linkage groups A2, C1, G, M, L25, and L26 were identified based on nonsimultaneous and simultaneous QTL analyses of individual markers (FIG. 1 and Table 2).

TABLE 2

Comparison of soybean genetic-marker linkage groups that had QTL affecting resistance to SCN races-1, -2, -3, -5, and -14. Each linkage group represents one QTL. G and M did not have independent effects on resistance

| SCN race | Linkage groups that have SCN-resistance QTL | | | | | |
|---|---|---|---|---|---|---|
| 1 | A2 | C1 | G | M | L25 | |
| 2 | | C1 | G | M | L25 | L26 |
| 3 | A2 | | G | M | | |
| 5 | | | G | M | L25 | |
| 14 | | | G | M | L25 | L26 |

Linkage groups A2, C1, G, and M correspond to those of the USDA-ISU molecular-marker linkage map (Shoemaker and Specht 1995) and were confirmed by comparing band sizes from probe and enzyme combinations in common between the two maps (Randy Shoemaker and Lisa Lorenzen, pers comm). Linkage groups L25 and L26 have not yet been associated with specific linkage groups on the public linkage map. The markers, pBLT65a, php02298b, php05354a, php02301a, pA567a, and pK79a, had the highest LOD scores at marker positions within groups A2, C1, G, M, L25, and L26, respectively. The QTL positions were estimated based on the relative magnitude of LOD scores at these and other markers shown in FIG. 1.

All six QTL were detected and mapped to an identical location in more than one of the five independent tests (SCN races) that were conducted. Each repeated detection and mapping of a QTL by an identical marker validated the statistical results and conclusions made from the other tests where that QTL was found.

The QTL on linkage-group M, was not independent of the QTL on linkage-group G. Both QTL accounted for the same variation for reaction to all five SCN races. The markers, php05354a and php02301a, associated with these QTL were highly significant for reaction to all SCN races when analyzed nonsimultaneously; however, when analyzed simultaneously, php05354a was significant and php02301a was nonsignificant for association with all five SCN races. The SCN race-3 results of these analyses are shown in Table 3.

TABLE 3

Test statistics from non-simultaneous analyses and simultaneous analyses for marker and QTL associations based on the log-transformed index-of-parasitism for SCN race-3. The coefficient of determination ($R^2$) is the estimated proportion of phenotypic variation explained by each source

| | Nonsimultaneous estimates | | | Simultaneous estimates | | |
|---|---|---|---|---|---|---|
| Source | $F^a$ | Prob > F | $R^2$ | F | Prob > F | $R^2$ |
| pBLT65a (A) | 65.03 | 0.0001 | 0.19 | 96.12 | 0.0001 | 0.16 |
| php05354a (G) | 178.76 | 0.0001 | 0.38 | 156.72 | 0.0001 | 0.27 |
| php02301a (M) | 42.88 | 0.0001 | 0.14 | 2.34 | 0.1273 | 0.00 |

$^a$Based on permutation tests, an F ≧ 10.5 was associated with a 95% probability for marker and QTL association Because php02301a was not significant in simultaneous analyses with php05354a for each of the five SCN races, php02301a was excluded from the final model for each SCN race when tested simultaneously with interactions. By excluding php02301a, the F statistics for php05354a increased substantially, and all remaining loci in each model and their all-way interactions were significant (Tables 4-8).

TABLE 4

Test statistics from simultaneous analysis with interaction for marker and QTL associations based on the log-transformed index-of-parasitism for SCN race-1. The coefficient of determination ($R^2$) is the estimated proportion of phenotypic variation explained by each source

| Source | Degrees of Freedom | Mean Square | F Value | Prob > F | $R^2$ |
|---|---|---|---|---|---|
| Full model | 15 | 9.46 | 8.24 | 0.0001 | 0.33 |
| php05354a (G) | 1 | 80.56 | 70.17 | 0.0001 | 0.19 |
| pBLT65a (A2) | 1 | 13.21 | 11.50 | 0.0008 | 0.03 |
| pA567a (L25) | 1 | 9.19 | 8.01 | 0.0050 | 0.02 |
| php02298b(C1) | 1 | 5.20 | 4.53 | 0.0343 | 0.01 |
| GxA2xL25xC1 | 11 | 3.07 | 2.67 | 0.0029 | 0.08 |
| Error | 248 | 1.15 | | | |

TABLE 5

Test statistics from simultaneous analysis with interaction for marker and QTL associations based on the log-transformed index-of-parasitism for SCN race-2. The coefficient of determination ($R^2$) is the estimated proportion of phenotypic variation explained by each source

| Source | Degrees of Freedom | Mean Square | F Value | Prob > F | $R^2$ |
|---|---|---|---|---|---|
| Full model | 15 | 10.64 | 10.93 | 0.0001 | 0.42 |
| php05354a (G) | 1 | 96.87 | 99.53 | 0.0001 | 0.26 |
| pA567a (L25) | 1 | 15.50 | 15.92 | 0.0001 | 0.04 |
| pK079a (L26) | 1 | 12.29 | 12.63 | 0.0005 | 0.03 |
| php02298b (C1) | 1 | 6.86 | 7.06 | 0.0085 | 0.02 |
| GxL25xL26xC1 | 11 | 3.49 | 3.58 | 0.0001 | 0.10 |
| Error | 222 | 0.97 | | | |

TABLE 6

Test statistics from simultaneous analysis with interaction for marker and QTL associations based on the log-transformed index-of-parasitism for SCN race-3. The coefficient of determination ($R^2$) is the estimated proportion of phenotypic variation explained by each source

| Source | Degrees of Freedom | Mean Square | F Value | Prob > F | $R^2$ |
|---|---|---|---|---|---|
| Full model | 3 | 169.98 | 384.78 | 0.0001 | 0.81 |
| php05354a (G) | 1 | 269.03 | 608.99 | 0.0001 | 0.43 |
| pBLT65a (A2) | 1 | 174.32 | 394.60 | 0.0001 | 0.28 |
| GxA2 | 1 | 157.31 | 356.08 | 0.0001 | 0.25 |
| Error | 273 | 0.44 | | | |

TABLE 7

Test statistics from simultaneous analysis with interaction for marker and QTL associations based on the log-transformed index-of-parasitism for SCN race-5. The coefficient of determination ($R^2$) is the estimated proportion of phenotypic variation explained by each source

| Source | Degrees of Freedom | Mean Square | F Value | Prob > F | $R^2$ |
|---|---|---|---|---|---|
| Full model | 3 | 51.72 | 34.46 | 0.0001 | 0.38 |
| php05354a (G) | 1 | 108.61 | 72.37 | 0.0001 | 0.26 |
| pA567a (L25) | 1 | 27.97 | 18.64 | 0.0001 | 0.07 |
| GxL25 | 1 | 32.72 | 21.80 | 0.0001 | 0.08 |
| Error | 171 | 1.50 | | | |

TABLE 8

Test statistics from simultaneous analysis with interaction for marker and QTL associations based on the log-transformed index-of-parasitism for SCN race-14. The coefficient of determination ($R^2$) is the estimated proportion of phenotypic variation explained by each source

| Source | Degrees of Freedom | Mean Square | F Value | Prob > F | $R^2$ |
|---|---|---|---|---|---|
| Full model | 7 | 12.92 | 10.56 | 0.0001 | 0.24 |
| php05354a (G) | 1 | 30.59 | 30.59 | 0.0001 | 0.10 |
| pA567a (L25) | 1 | 9.08 | 9.08 | 0.0029 | 0.03 |
| pK079a (L26) | 1 | 27.78 | 27.78 | 0.0001 | 0.09 |
| GxL25xL26 | 4 | 4.30 | 4.30 | 0.0022 | 0.06 |
| Error | 234 | 1.22 | | | |

Distortion in marker classes between php05354a and php02301a

In this population, 273 lines were homozygous and without missing data for the markers php05354a and php02301a on linkage-groups G and M, respectively. Having four possible homozygous classes for two markers combined, 68 lines per class were expected if normal segregation of alleles occurred. The actual and expected number of lines in these marker classes are shown in Table 9.

TABLE 9

Actual and expected number of lines in each of the homozygous classes for the marker combination php05354a and php02301a from linkage-groups G and M, respectively. The A allele came from BSR101 and the B allele came from PI 437.654

| php05354a/<br>php02301a | Actual<br># lines | Expected<br># lines |
|---|---|---|
| A/A | 88 | 68 |
| A/B | 79 | 68 |
| B/A | 5 | 68 |
| B/B | 101 | 68 |
| Total | 273 | 273 |

The class that had both php05354a alleles from PI 437.654 and both php02301a alleles from BSR101, included only five lines; substantially fewer than occurred in the other classes. Of those lines that had php05354a from the parent BSR101, about half (88 lines) received php02301a from BSR101 and half (79 lines) from PI 437.654, as would be expected between two independent loci. However, of the 106 lines that had the PI 437.654 allele at php05354a, 101 lines also had the PI 437.654 allele at php02301a (Table 9).

Apparently, the combination of the allele from PI 437.654 in the region of php05354a with the allele from BSR101 in the region of php02301a was deleterious to survival, and selection occurred during the development of the inbred lines. It cannot be distinguished whether this distortion in allele frequencies and the association of these two regions with SCN resistance were a result of pleiotropy, linkage of other genes to the SCN-resistance QTL, or a combination of both situations. However, and without intending to be limited by theory because this population was developed by single-seed descent without conscious selection, the distortion in allele frequencies is attributed to natural selection associated with particular genotypes on linkage groups G and M prior to the maturation of seed. It was not evident whether the loss of genotypes occurred in the gametophyte or after fertilization.

QTL Effects on SCN Resistance

The region on group M near php02301a was involved with SCN resistance to the extent that it was needed in lines carrying the resistance QTL on group G. However, because the loci on M and G were not independent of each other, the locus on group M was not significant when the loci on M and G were tested simultaneously.

The proportions of the phenotypic variation detected by the marker loci associated with the independent QTL on groups A2, G, C1, L25, and L26 for the five SCN races were represented by the coefficient of determination ($R^2$) in Tables 4-8. The $R^2$ values varied among QTL within each SCN race depending on the genetic effect of each QTL and the amount of recombination (source of error) between each QTL and the marker used to estimate that QTL's genotype.

The effects of the resistance QTL on the index-of-parasitism for each SCN race were estimated from the differences between the least-square phenotypic means of the homozygous marker classes associated with each QTL (Table 10).

TABLE 10

Index-of-parasitism least-square means for the homozygous classes (A and B) at individual markers that were associated with QTL for resistance to SCN races-1, -2, -3, -5, and -14. Least-square means were estimated from log-transformed data and converted back to a linear scale. Class-A came from BSR101 and class-B came from PI 437.654. $\overline{A} - \overline{B}$ represents the estimated effect of each locus on the index-of-parasitism.

| Marker | $\overline{A}$ | $\overline{B}$ | $\overline{A} - \overline{B}$ |
|---|---|---|---|
| SCN race-1 | | | |
| pBLT65a (A2) | 24.3 | 14.7 | 9.6 |
| php05354a (G) | 34.9 | 10.1 | 24.8 |
| pA567a (L25) | 23.3 | 16.4 | 6.9 |
| php02298b (C1) | 22.2 | 16.2 | 6.0 |
| SCN race-2 | | | |
| php05354a (G) | 57.0 | 13.9 | 43.1 |
| pA567a (L25) | 37.5 | 21.4 | 16.1 |
| pK79a (L26) | 36.3 | 22.1 | 14.2 |
| php02298b (C1) | 34.2 | 23.5 | 10.7 |
| SCN race-3 | | | |
| pBLT65a (A) | 41.5 | 7.3 | 34.2 |
| php05354a (G) | 50.9 | 5.9 | 45.0 |
| SCN race-5 | | | |
| php05354a (G) | 54.1 | 9.9 | 44.2 |
| pA567a (L25) | 36.0 | 15.3 | 20.7 |
| SCN race-14 | | | |
| php05354a (G) | 26.9 | 11.3 | 15.6 |
| pA567a (L25) | 22.3 | 13.9 | 8.4 |
| pK79a (L26) | 26.4 | 11.6 | 14.8 |

The greater the difference between least-square phenotypic means of the two marker classes, the greater effect that QTL had on reducing the rate of SCN infection.

The QTL on group G was the only QTL involved with all five SCN races, and had the largest estimated effect on resistance to every race. The QTL on group L25 was involved with four of the SCN races, and the QTL on groups A2, C1, and L26 were each involved with resistance to two SCN races. The markers used to estimate the QTL effects were within 5 cM of the QTL except on L25 where the distance between the marker and QTL was about 20 cM (FIG. 1). The QTL effects for all the loci except L25 were therefore estimated on a comparable basis and should be relatively accurate. The effect of the QTL on L25 was underestimated relative to the other QTL due to the increased error associated with the large recombination distance between the marker and QTL. The fact that the QTL on L25 was detected and had significant effects estimated for four different SCN races using a relatively distant marker indicates that this QTL probably had greater effects than estimated and was a substantial contributor to resistance.

Figure 2:
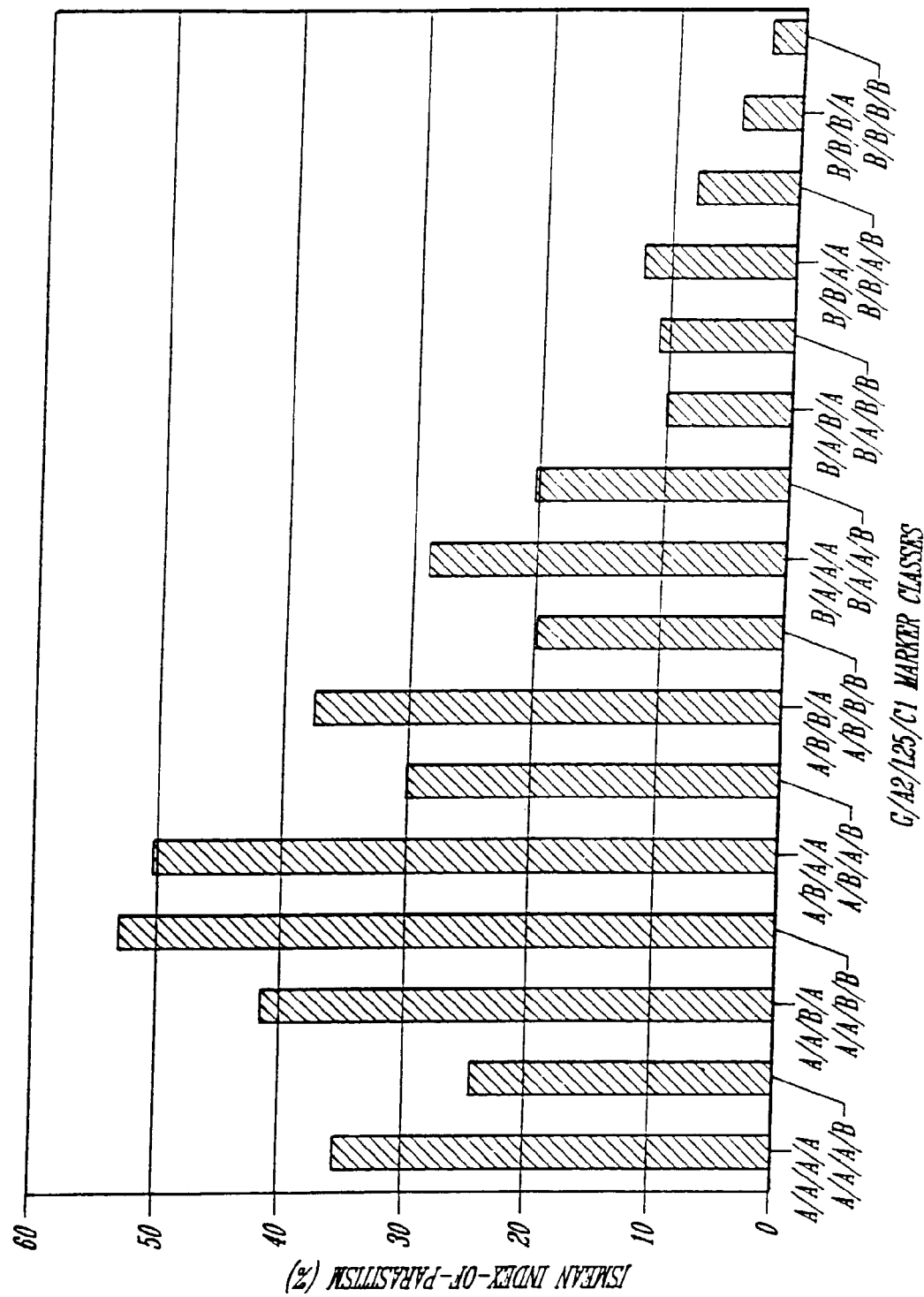
FIG. 2 shows SCN race-1 least-square mean index-of-parasitism scores for the homozygous marker classes of php05354a, pBLT65a, pA567a, and php02298b on linkage groups G, A2, L25, and C1, respectively. "A" and "B" scores represent BSR101 and PI 437.654 homozygous marker types, respectively.
Figure 3:
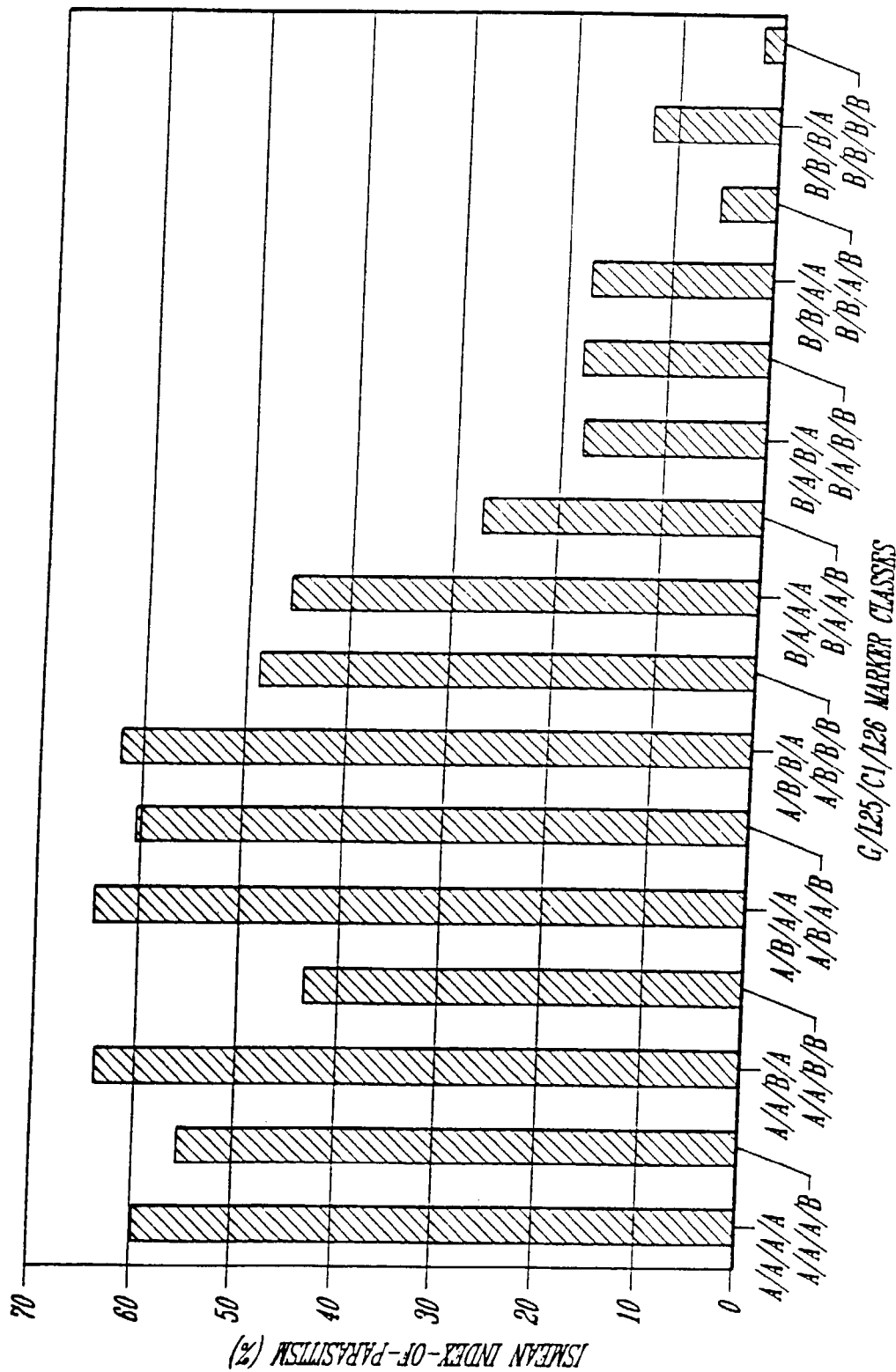
FIG. 3 shows SCN race-2 least-square mean index-of-parasitism scores for the homozygous marker classes of php05354a, pA567a, php02298b, and pK79a on linkage groups G, L25, C1, and L26, respectively. "A" and "B" scores represent BSR101 and PI 437.654 homozygous marker types, respectively.
Figure 4:
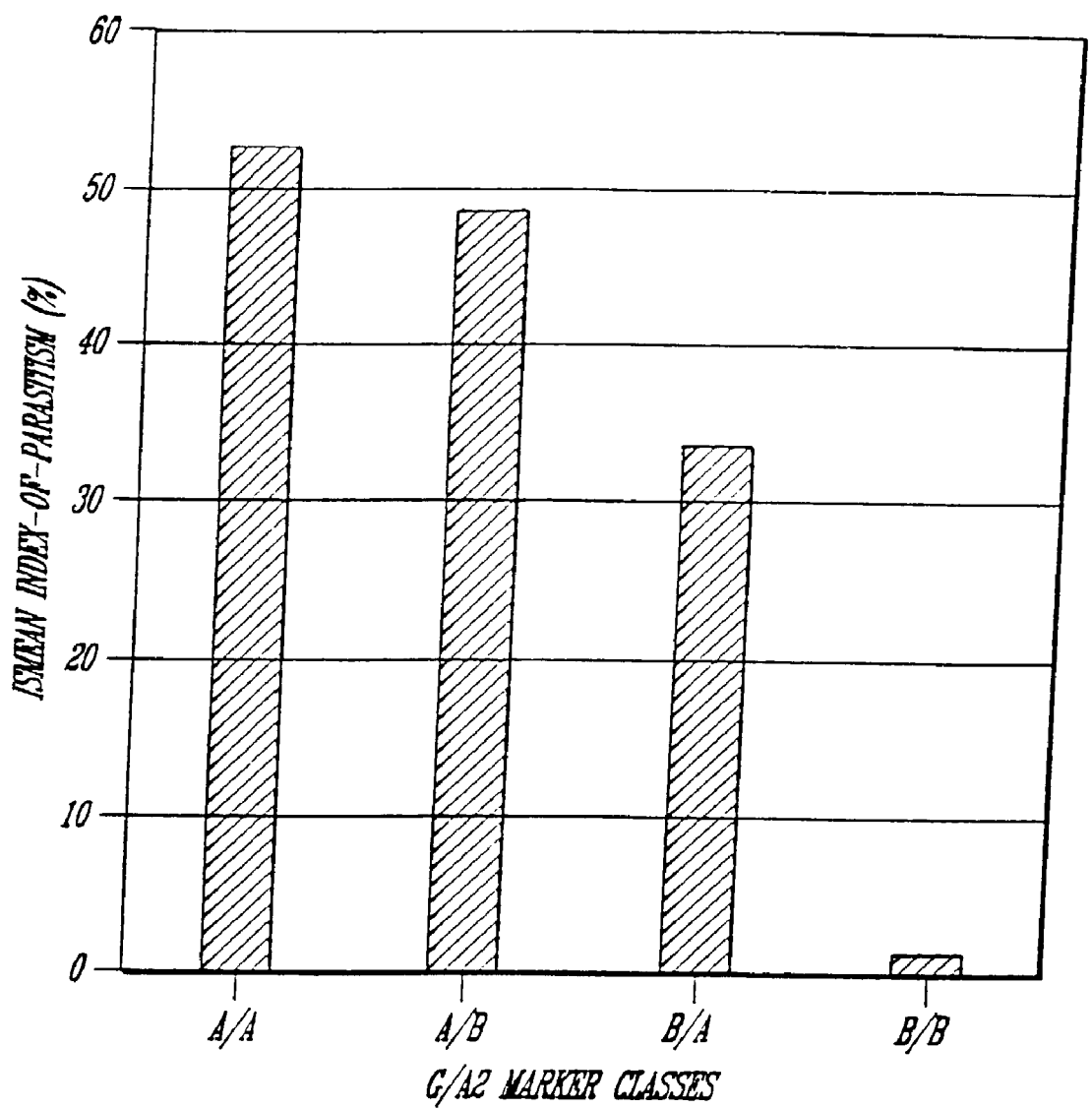
FIG. 4 shows SCN race-3 least-square mean index-of-parasitism scores for the homozygous marker classes of php05354a and pBLT65a, on linkage groups G and A2, respectively. "A" and "B" scores represent BSR101 and PI 437.654 homozygous marker types, respectively.
Figure 5:
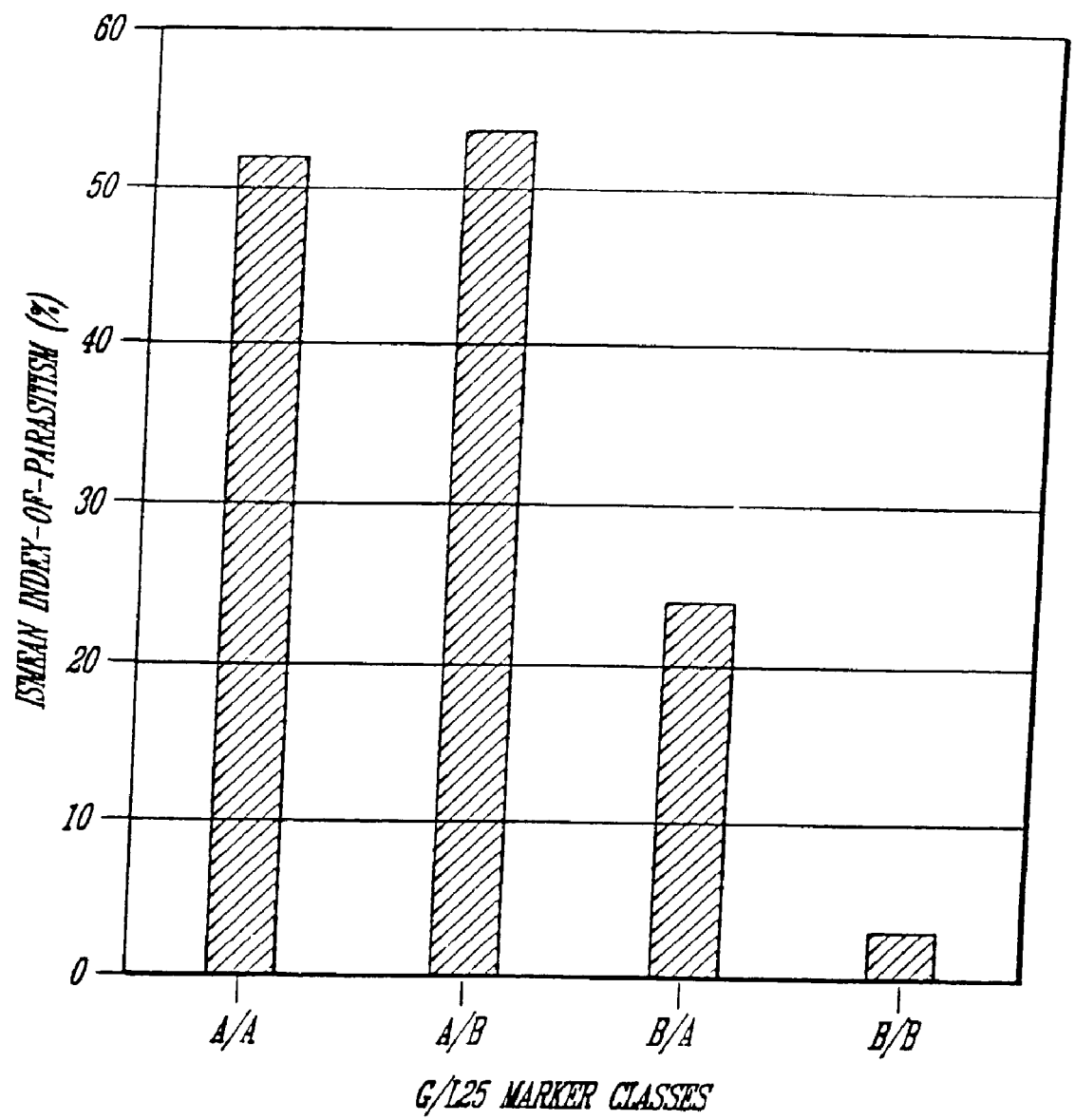
FIG. 5 shows SCN race-5 least-square mean index-of-parasitism scores for the homozygous marker classes of php05354a and pA567a on linkage groups G and L25, respectively. "A" and "B" scores represent BSR101 and PI 437.654 homozygous marker types, respectively.
Figure 6:
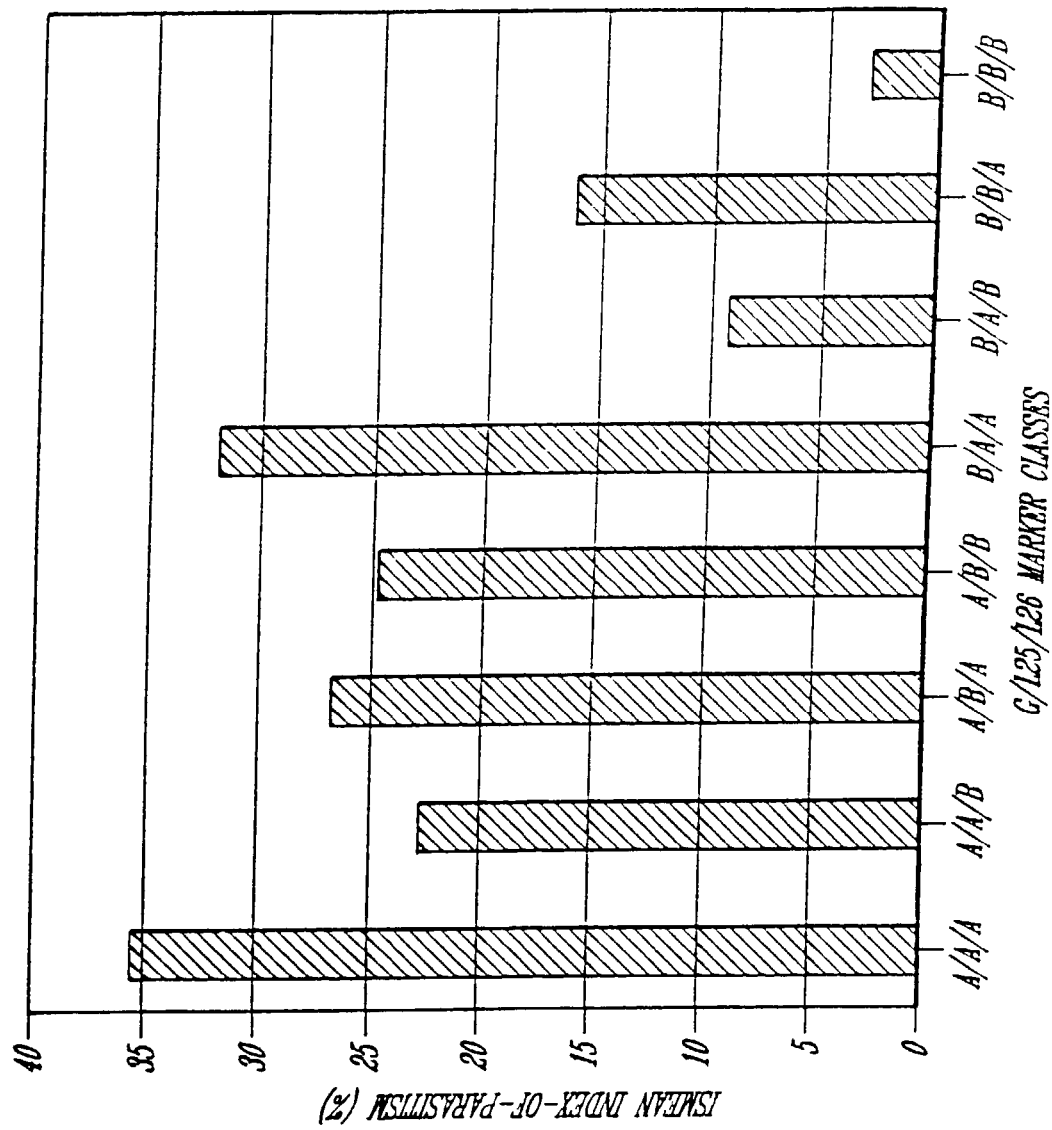
FIG. 6 shows SCN race-14 least-square mean index-of-parasitism scores for the homozygous marker classes of php05354a, pA567a, and pK79a on linkage groups G, L25, and L26, respectively. "A" and "B" scores represent BSR101 and PI 437.654 homozygous marker types, respectively.

Resistance to any of the five SCN races appeared to be a result of the combined effects of the QTL involved for each race. The interactions among the QTL were statistically significant for each race (Tables 4-8). The effects of these QTL interactions on resistance to each SCN race is presented in FIGS. 2-6, where the classes of lines that had all the QTL-linked marker alleles from PI 437.654 had the least amount of SCN infection and were most likely to have resistance (IP<2). Partial resistance was indicated for SCN races-3 and -5 by having the QTL on group G alone (FIGS. 4-5). For SCN races-1, -2, and -14, which had more than two QTL each, partial resistance was indicated by having the QTL on group G in combination with one or more (but not all) other QTL (FIGS. 2, 3, and 6). Without intending to be limited by theory, these data indicate that in the absence of the complement of QTL alleles affecting resistance to each SCN race, partial resistance may be obtained by fewer QTL when the resistance allele is present at the QTL on group G.

Discussion

SCN race-3 was found more frequently than other races in Tennessee, Missouri, Ohio, Illinois, and Iowa, while other SCN races were found more often in southern states (Anand et al. 1994). Race-3 is generally considered the predominant race in much of the soybean production areas of North America. Consequently, much attention has been given to the genetics and breeding for resistance to SCN race-3. Less effort has been made to study and breed for resistances to SCN races-1, -2, -5, and -14. Because shifts in the race classification of SCN populations are likely to occur in response to natural selection on soybean cultivars resistant to one or a few SCN races (Triantaphyllou 1975; McCann et al. 1982; Young 1984; Anand et al. 1994), a broad spectrum of SCN resistance needs to be incorporated into commercial varieties to help prevent and respond to these shifts. Five independent loci in the soybean PI 437.654 associated with resistance to SCN races-1, -2, -3, -5, and -14 were genetically mapped. These five loci can provide more SCN resistance than presently found in any commercial soybean variety.

Sources of SCN Race-3 Resistance

Because all progeny from crosses between Peking and PI 437.654 are resistant to SCN race-3 (Anand 1985; Myers and Anand 1991), the race-3 resistance loci mapped here should be in Peking. By the same logic, because all progeny from crosses between Peking and PI 90763 are resistant to SCN race-3 (Rao-Arelli and Anand 1988; Rao-Arelli et al. 1992a), the race-3 resistance loci mapped here should also be in PI 90763.

Although three loci individually associated with SCN race-3 resistance were mapped, only the two loci on groups A2 and G accounted for the genetic variation. Also, the number of race-3 resistant lines (55) found in this population was not significantly different ($X^2$=0.2, P=0.7-0.5) from the 52 lines expected based on the allele frequencies at the nearest markers to the QTL on groups A2 and G. Although these two resistance loci should be in Peking and PI 90763, it is not clear whether or not those two soybean varieties require a third locus for resistance. Rao-Arelli et al. (1992a) used phenotypic segregation ratios of resistant and susceptible progeny to estimate the number of SCN race-3 resistance loci segregating in $F_2$ and $F_3$ populations of Peking X Essex and PI 90763 X Essex. Their $F_2$ data did not allow them to reject either of their two hypotheses that there are one dominant and two recessive resistance loci, or only two recessive resistance loci in Peking and PI 90763. Their $F_3$ data allowed them to reject both these hypotheses, not because of the number of resistance lines, but because of the greater than expected number of segregating lines. This leaves open the possibility that Peking and PI 90763 require only the two loci we found in PI 437.654 for SCN race-3 resistance.

Matson and Williams (1965) reported a dominant SCN resistance locus, which they named $Rhg_4$, with about 0.35% recombination from the I locus in Peking. In the present studies the I locus were mapped to approximately the same distance from a resistance QTL on linkage group A2 (FIG. 1) as Matson and Williams estimated in Peking. Therefore $Rhg_4$ was assigned to this resistance locus on the present map. The gene action of any resistance locus could not be confirmed because the population used was inbred.

Caldwell et al. (1960) identified three recessive loci, $rhg_1$, $rhg_2$, and $rhg_3$, in Peking for SCN race-1 resistance [race identified after publication (Rao-Arelli et al. 1991a)]. Later, Rao-Arelli et al. (1992a) assigned $rhg_1$ and $rhg_2$ to two recessive loci for SCN race-3 resistance which they concluded were in Peking, and selected $rhg_2$ to be the recessive resistance locus also found in the soybean PI 88788. Because different SCN races were used and no common reference markers existed, the $rhg_1$ and $rhg_2$ designations may have been assigned to different loci in each study. It is unknown whether the same loci govern both SCN race-1 and race-3 resistance. In the present studies a race-3 resistance locus in PI 437.654 (also in Peking) was found on group G, but $rhg_1$ and $rhg_2$ cannot be distinguished based on the assignment of Rao-Arelli et al. (1992a) without knowing which one is in PI 88788. Therefore, a locus name was not assigned to the QTL on group G or any other QTL.

Sources of SCN Race-5 Resistance

Anand and Rao-Arelli (1989) concluded that for SCN race-5 resistance, Peking and PI 90763 each expressed two recessive genes when crossed with PI 88788 and Forrest, respectively, and one dominant gene each when crossed to each other. Anand (1994) found that PI 90763, when crossed with the variety Essex, likely expressed two recessive genes and one dominant gene for SCN race-5 resistance. Myers and Anand (1991) showed that the $F_1$, $F_2$, and $F_3$ populations from crosses of Peking and PI 90763 to PI 437.654 did not segregate and were all resistant to SCN race-5, concluding that PI 437.654 had the same SCN race-5 resistance loci as Peking and PI 90763.

In the current studies, two QTL in PI 437.654 were found for resistance to SCN race-5 and the number of lines (34) that had resistance to SCN race-5 (IP<2) in this population was not significantly different ($X^2$=0.5, P=0.5-0.3) from the 38 lines expected based on the allele frequencies at the nearest markers to the QTL on groups G and L25. According to the findings of Myers and Anand (1991), these two QTL for SCN race-5 resistance should also be in Peking and PI 90763.

Comparison to Previous Mapping Studies for SCN Race-3

This is the first report from any source of genetic markers linked to resistance QTL in soybean for SCN races-1, -2, -5, and -14; however, reports have been made of genetic markers linked to resistance QTL for SCN race-3 from sources other than PI 437.654.

Keim et al. (1990) placed pT153 (pT153 equals pT155 in band pattern and two linkage-map locations; P. Keim, pers comm), I, and pA111 in this order with distances of 14 and 22 map units, respectively, on group A (group A=group A2). In the current studies the order of these three markers was the same with distances of 7 and 15 cM, respectively. Weisemann et al. (1992) placed pBLT24, I, and pBLT65 in this order with distances of 4.4 and 4.0% recombination, respectively. These markers were ordered in the current studies as pBLT24, pBLT65, and I at distances of 1.5 and 0.6 cM, respectively, and distances between markers were expected to vary according to population, number of markers, and method of calculation; however, the order of markers is likely to be the same among different populations of the same or closely related species. Without intending to be limited by theory, the different order found may be due to marker-scoring errors in one or both of these experiments or to a short chromosomal inversion in one or the other population.

Using PI 209.332 as the source of SCN resistance, Concibido et al. (1994) found pA85 on group A significantly associated with SCN race-3 resistance. Additionally, they noted that pA111 on group A was not associated with SCN resistance. They also found that the/locus on group A showed some association with resistance but at a level that was not statistically significant. The results in the current studies with these three markers clearly placed I closest to $Rhg_4$, while pA85a and pA111a were farther from $Rhg_4$ (FIG. 1). In the present studies six markers were placed between pA85a and the I locus for a total distance of 42.4 cM. Concibido et al. (1994) had 10.9 cM between pA85 and the I locus with no additional markers between them. For a more direct comparison in the present studies, the markers between pA85a and the/locus were removed from the present data and the distance was then estimated to be 30.1 cM. Without intending to be limited by theory, the greater recombination between these two markers in the instant experiment may have contributed to pA85a not being associated with a QTL. However, given the non-significant QTL association of the/locus found by Concibido et al. (1994), it may be the QTL found by them in PI 209.332 on group A is a different locus from $Rhg_4$ found by Matson and Williams (1965) in Peking and found in the instant studies in PI 437.654.

Concibido et al. (1994) reported pK69 on linkage group G associated with SCN race-3 resistance in PI 209.332. This marker was also found to be associated with a resistance locus on group G in the present studies (FIG. 1). pK69 had been an end marker of group G (formerly linkage group D, Diers et al. 1992), and in the instant studies the resistance locus was found to be outside this linkage group of markers. In the current move five new RFLP markers beyond pK69, two of which were approximately 5 cM apart and flanked the resistance locus (FIG. 1).

Concibido et al. (1994) also reported the marker pB32 on linkage group K associated with SCN race-3 resistance in PI 209.332. It is believed pB32 can hybridize to four loci, two of which were mapped in the instant work to linkage groups J and K and were not associated with SCN race-3 resistance in PI 437.654. Without intending to be limited by theory, they may have used one of the other two possible marker-loci for this probe. Their pB32 marker was linked to a pK417 marker, which was less significantly associated with SCN resistance. pK417 markers have been mapped to linkage groups A, K, and M on the USDA/Iowa State University public RFLP map (Randy Shoemaker, pers comm). pK417 was not used in the present work because it was monomorphic, but comparing the map disclosed herein with the USDA/ISU public map, the pK417 marker on group A may be near enough to detect linkage to the SCN resistance locus on that group.

PI 209.332 may have a different mode of SCN race-3 resistance than PI 437.654. Rao-Arelli et al. (1993) reported that the SCN race-3 resistance in PI 209.332 is most likely controlled by two loci, one dominant and one recessive. If so, evidence from Concibido et al. (1994) indicates those two loci are on linkage groups A and G, and the pB32 marker used by them may therefore go to group A. Without intending to be limited by theory, if PI 209.332 has three SCN race-3 resistance loci and the pB32 marker used by Concibido et al. is on linkage group K, then PI 209.332 and PI 437.654 may differ, not only by the position of the QTL on group A, but also by PI 209.332 having a race-3 resistance locus on K.

Again, without intending to be limited by theory, these differences between PI 209.332 and PI 437.654 may be due to different loci for SCN race-3 resistance or to differences in the SCN race isolates used in these studies. Although both isolates were classified as race-3 by their behavior on the standard soybean differentials, they may have been sufficiently different to induce responses from different resistance loci.

Marker-Assisted Selection

It is believed that the markers disclosed herein (FIG. 1), or similarly placed markers on groups A2, C1, G, M, L25, and L26, can be used in soybean breeding for marker-assisted selection of resistance to SCN races 1, 2, 3, 5, and 14. However, markers should not be needed to select for the QTL on group M because, in this population, the lines that had the resistant-parent marker allele on group G almost always had the resistant-parent marker allele on group M. The allele on group M associated with resistance was naturally selected in lines with the resistance allele on group G.

Selecting for resistance based on two markers that flank each QTL should be more reliable than selections based on one marker linked to each QTL. Flanking-marker selection reduces the possibility of not detecting recombination between a marker and the QTL, and consequently, reduces the probability of making a Type-I error (selecting a line that is susceptible). However, when markers are closely linked to the QTL, as were found in the present experiment for every QTL except on group L25, single-marker selections at each locus may have an acceptable Type-I error rate, substantially reduce the amount of laboratory work, and also reduce the Type-II error rate (not selecting resistant lines).

In this mapping population, all 44 lines with the PI 437.654 marker type at the four nearest RFLP markers flanking the resistance loci on A2 and G were resistant to SCN race-3. By comparison, all 50 lines with the PI 437.654 marker type at the individual markers nearest the QTL on A2 and G were resistant to SCN race-3. If marker-assisted selection for SCN race-3 resistance were conducted in this population using two (single) markers instead of four (flanking), less laboratory work would be needed, no Type-I error would occur, and fewer Type-II errors would occur with the selection of six additional resistant lines. Of 55 resistant lines in this population, five would be missed using single-marker selection and eleven would be missed using flanking-marker selection. No Type-I error in selection would be made by either method.

Given that PI 437.654 and Peking have the same resistance loci for SCN race-3, markers linked to these loci should be useful for marker-assisted selection in germplasm related to either source. However, PI 88788, another common source of SCN race-3 resistance, lacks a resistance allele on either group A2 or G and has a resistance allele at a different locus than does Peking (Rao-Arelli et al. 1992a) and PI 437.654. While this does not preclude using the method of the invention in 88788, the unique locus in PI 88788 needs to be genetically mapped to identify the necessary markers for more complete marker-assisted selection of all SCN race-3 resistance loci in populations related to PI 88788.

Example 2

Positional Cloning

Markers linked to each of the six mapped QTL for SCN resistance are used in positional cloning of genes that reside within those QTL. Positional cloning first involves creating a physical map of a contig (contiguous overlapping of cloned DNA inserts), in the genomic region encompassing one or more marker loci and the target gene. The target gene is then identified and isolated within one or more clones residing in the contig. Having a clone of a gene allows it to be used in genetic studies, transformation, and the development of novel phenotypes.

Mapped SCN markers, especially those most closely linked to the QTL and those that flank the resistance QTL on both sides are used to identify homologous clones from soybean genomic libraries, including, for example, soybean genomic libraries made in bacterial artificial chromosomes (BAC), yeast artificial chromosomes (YAV), or P1 bacteriophage. These types of vectors are preferred for positional cloning because they have the capacity to carry larger DNA inserts than possible with other vector technologies. These larger DNA inserts allow the researcher to move physically farther with each overlap of clones along the chromosome. At lease two such libraries, one BAC (Marek and Shoemaker 1996) and one YAC (Zhu et al. 1996), have been constructed and are available for positional cloning efforts in soybean. Mapped SCN markers are used as DNA probes to hybridize and select homologous genomic clones from such libraries. Alternatively, the DNA of mapped marker clones are sequenced to design PCR primers that amplify and therefore identify homologous genomic clones from such libraries. Either method is used to identify large-insert soybean clones that is then used to start or finish a contig constructed in chromosome walking to clone an SCN resistance QTL.

As examples, the positional cloning strategy was successfully used to clone the cystic fibrosis gene in humans (Rommens et al. 1989), an omega-3 desaturase gene in *Arabidopsis* (Arondel et al. 1992), a protein kinase gene (Pto) conferring fungal resistance in tomato (Martin et al. 1993), and the isolation of a YAC clone containing the jointless gene that suppresses abscission of flowers and fruit in tomato (Zhang et al. 1994). For reviews on position cloning, see Wicking and Williamson (1991), Gibson and Somerville (1993), and Parrish and Nelson (1993).

REFERENCES

Anand S C (1984) Identification of additional soybean germplasm with resistance to race 3 of the soybean cyst nematode. Plant Dis 68:593-595

Anand S C (1985) Sources of resistance to the soybean cyst nematode. In Lamberti F, Taylor C E (eds) Cyst nematodes. NATO advanced study institute series. Plenum Press, New York, pp. 269-276

Anand S C (1991) Registration of soybean germplasm line S88-2036 having multiple-race soybean cyst nematode resistance. Crop Sci 31:856

Anand S C (1994) Genetic diversity for resistance to *Heterodera glycines* race 5 in soybean. J Nematol 26:76-79

Anand S C, Rao-Arelli A P (1989) Genetic analyses of soybean genotypes resistant to soybean cyst nematode race 5. Crop Sci 29:1181-1184

Anand S C, Sharma S B, Rao-Arelli A P, Wrather J A (1994) Variation in parasitic potential of *Heterodera glycines* populations. Crop Sci 34:1452-1454

Arondel V, Lemieux B, Hwang I, Gibson S, Goodman H M, Somerville C R (1992) Map-based cloning of a gene controlling omega-3 fatty acid desaturation in *Arabidopsis*. Science 258:1353-1355

Baltazar B M, Mansur L (1992) Identification of restriction fragment length polymorphisms (RFLPs) to map soybean cyst nematode resistance genes in soybean. Soybean Genet Newslett 19:120-122

Box G E P, Draper N R (1987) Adequacy of estimation and the use of transformation: In Empirical model-building and response surfaces. Joh Wiley & Sons, Inc., New York, pp. 268-291

Caldwell B E, Brim C A, Ross J P (1960) Inheritance of resistance of soybeans to the cyst nematode, *Heterodera glycines*. Agron J 52:635-636

Concibido V C, Denny R L, Boutin S R, Hautea R, Orf J H, Young N D (1994) DNA marker analysis of loci underlying resistance to soybean cyst nematode (*Heterodera glycines* Ichinohe). Crop Sci 34:240-246

Diers B W, Keim P, Fehr W R, Shoemaker R C (1992) RFLP analysis of soybean seed protein and oil content. Theor Appl Genet 83:608-612

Gibson S, Somerville C (1993) Isolating plant genes. Trends Biotech 11(7):306-313

Golden A M, Epps J M, Riggs R D, Duclos L A, Fox J A, Bernard R L (1970) Terminology and identity of infraspecific forms of the soybean cyst nematode (*Heterodera glycines*). Plant Dis Rep 54:544-546

Hartwig E E (1985) Breeding productive soybeans with resistance to the soybean cyst nematode. In: Shibles R (ed) Proceedings World Soy Res Conf III, Westview Press, Boulder, Colo., pp. 394-399

Keim P, Beavis W D, Schupp J M, Baltazar B M, Mansur L, Freestone R E, Vahedian M, Webb D M (1994) RFLP analysis of soybean breeding populations: I. Genetic structure differences due to inbreeding methods. Crop Sci 34:55-61

Keim P, Diers B W, Olson T C, Shoemaker R C (1990) RFLP mapping in soybean: association between marker loci and variation in quantitative traits. Genetics 126:735-742

Keim P, Olson T C, Shoemaker R C (1988) A rapid protocol for isolating soybean DNA. Soybean Genet Newslett 15:150-152

Keim P, Shoemaker R C (1988) Construction of a random recombinant DNA library that is primarily single copy sequences. Soybean Genet Newsl 15:147-148

Keim P, Shoemaker R C, Palmer R G (1989) Restriction fragment length polymorphism diversity in soybean. Theor Appl Genet 77:786-792

Knapp S J, Bridges W C, Liu B-H (1992) Mapping quantitative trait loci using nonsimultaneous and simultaneous estimators and hypothesis tests. In Beckmann J S, Osborn T C (eds) Plant genomes: methods for genetic and physical mapping. Kluwer Academic Publishers, The Netherlands, pp. 209-237

Lande R, Thompson R (1990) Efficiency of marker-assisted selection in the improvement of quantitative traits. Genetics 124:743-756

Lander E S, Botstein D (1986) Strategies for studying heterogeneous genetic traits in humans by using a linkage map of restriction fragment length polymorphisms. Proc Natl Acad Sci USA 83:7353-7357

Lander E S, Botstein D (1989) Mapping Mendelian factors underlying quantitative traits using RFLP linkage maps. Genetics 121:185-199

Landry B S, Hubert N, Etoh T, Harada J J, Lincoln S E (1991) A genetic map for *Brassica napus* based on restriction fragment length polymorphisms detected with expressed DNA sequences. Genome 34:543-552

Lincoln S E, Daly M J, Lander E S (1993) MAPMAKER/EXP. Whitehead Institute of Biomedical Research, Cambridge, Mass.

Lincoln S E, Lander E S (1990) MAPMAKER/QTL. Whitehead Institute of Biomedical Research, Cambridge, Mass.

Mansur L M, Carriquiry A L, Rao-Arelli A P (1993) Generation mean analysis of resistance to race 3 of soybean cyst nematode. Crop Sci 33:1249-1253

Marek L F, Shoemaker R C (1996) Construction and size characterization of a bacterial artificial chromosome (BAC) library from soybean. Soybean Genet Newslett 23:126-129

Martin G B, Brommonschenkel S H, Chunwongse J, Fraary A, Ganal M W, Spivey R, Wu T, Earle E D, Tanksley S D (1993) Map based cloning of a protein kinase gene conferring disease resistance in tomato. Science 262: 1432-1436

Matson A L, Williams L F (1965) Evidence of a fourth gene for resistance to the soybean cyst nematode. Crop Sci 5:477

McCann J, Luedders V D, Dropkin V H (1982) Selection and reproduction of soybean cyst nematodes on resistant soybeans. Crop Sci 22:78-80

Mulrooney R P (1988) Soybean disease loss estimate for southern United States in 1987. Plant Dis 72:915

Murray M, Thompson W F (1980) Rapid isolation of high-molecular-weight plant DNA. Nucleic Acids Res 8:4321-4325

Myers G O, Anand S C (1991) Inheritance of resistance and genetic relationships among soybean plant introductions to races of soybean cyst nematode. Euphytica 55:197-201

Nelson R L, Amdor P J, Orf J H, Cavins J F (1988) Evaluation of the USDA soybean germplasm collection: maturity groups 000 to IV (PI 427.136 to PI 445.845). USDA-ARS Tech Bull 1726

Niblack T L, Norton D C (1992) Soybean yield losses due to *Heterodera glycines* in Iowa. Plant Dis 76:943-948

Parrish J E, Nelson D L (1993) Methods for finding genes a major rate-limiting step in positional cloning. GATA 10(2): 29-41

Riggs R D, Schmitt D P (1988) Complete characterization of the race scheme for *Heterodera glycines*. J Nematol 20:392-395

Rao-Arelli A P, Anand S C (1988) Genetic relationships among soybean plant introductions for resistance to race 3 of soybean cyst nematode. Crop Sci 28:650-652

Rao-Arelli A P, Anand S C, Wrather J A (1991a) Additional dominant gene in PI 88.788 conferring resistance to soybean cyst nematode race 3. Soybean Genet Newslett 18:221-224

Rao-Arelli A P, Anand S C, Wrather J A (1992a) Soybean resistance to soybean cyst nematode race 3 is conditioned by an additional dominant gene. Crop Sci 32:862-864

Rao-Arelli A P, Clark K M, Owen P A (1993) Inheritance of soybean cyst nematode resistance genes in soybean germplasm. In Agronomy abstracts. ASA, Madison, Wis., p. 100

Rao-Arelli A P, Matson K W, Anand S C (1991b) A rapid method for inoculating soybean seedlings with *Heterodera glycines*. Plant Dis 75:594-595

Rao-Arelli A P, Wrather J A, Anand S C (1992b) Genetic diversity among isolates of *Heterodera glycines* and sources of resistance in soybeans. Plant Dis 76:894-896

Rommens J M, Iannuzzi M C, Kerem B-S, Drumm M L, Melmer G, Dean M, Rozmahel R, Cole J L, Kennedy D, Hidaka N, Zsiga M, Buchwald M, Riordan J R, Tsui L-C, Collins F S (1989) Identification of the cystic fibrosis gene: chromosome walking and jumping. Science 245:1059-1065

Shoemaker R C, Specht J E (1995) Integration of the soybean molecular and classical genetic linkage groups. Crop Sci 35:435-446

Tachibana H, Voss B K, Fehr W R (1987) Registration of BSR101 soybean. Crop Sci 27:612

Triantaphyllou A C (1975) Genetic structure of races of *Heterodera glycines* and inheritance of ability to reproduce on resistant soybeans. J Nematol 7:356-364

Weisemann J M, Matthews B F, Devine T E (1992) Molecular markers located proximal to the soybean cyst nematode resistance gene, $Rhg_4$. Theor Appl Genet 85:136-138

Weiss M G (1970) Genetic linkage in soybeans: linkage group VII. Crop Sci 10:627-629

Wicking C, Williamson B (1991) From linked marker to gene. Trends Genet 7(9):288-293

Winstead N N, Skotland C B, Sasser J N (1955) Soybean-cyst nematode in North Carolina. Plant Dis Rep 39:9-11

Young L D (1982) Reproduction of differentially selected soybean cyst nematode populations on soybeans. Crop Sci 22:385-388

Young L D (1984) Changes in the reproduction of *Heterodera glycines* on different lines of *Glycine max*. J Nematol 16:304-309

Zhang H-B, Martin G B, Tanksley S D, Wing R A (1994) Map-based cloning in crop plants: tomato as a model system II. Isolation and characterization of a set of overlapping yeast artificial chromosomes encompassing the jointless locus. Mol Gen Genet 244:613-621

Zhu, T, Shi L, Funke R P, Gresshoff P M, Keim P (1996) Characterization and application of soybean YACs to molecular cytogenetics. Mol Gen Genet 252:483-488

What is claimed is:

1. A method of selecting at least one soybean plant by marker assisted selection of a quantitative trait locus ("QTL") associated with soybean cyst nematode resistance, wherein said QTL is localized to a chromosomal interval on linkage group G above the marker pk69 and on or below the marker php02366, the sequence of marker php02366 having been deposited with the ATCC as Accession Number 69934, said method comprising testing at least one marker on said chromosomal interval for said QTL and selecting said soybean plant comprising said QTL.

2. The method of claim 1, wherein said selected soybean plant is used in a cross to introgress said QTL into progeny soybean germplasm.

3. The method of claim 1, further comprising confirming soybean cyst nematode resistance in said soybean plant by challenging said plant with soybean cyst nematodes and scoring the resulting phenotype for soybean cyst nematode resistance.

4. The method of claim 1, wherein said selected soybean plant is the progeny of a cross of two parents, wherein at least one of the parents is resistant to soybean cyst nematode.

* * * * *